US009435513B2

(12) United States Patent
Tamura et al.

(10) Patent No.: US 9,435,513 B2
(45) Date of Patent: Sep. 6, 2016

(54) LIGHT SOURCE DEVICE HAVING OPTICAL MEMBERS FOR CHANGING ONE OR MORE CHARACTERISTICS OF EXCITATION LIGHT FROM AN EXCITATION LIGHT SOURCE

(71) Applicant: OLYMPUS CORPORATION, Tokyo (JP)

(72) Inventors: Kazuaki Tamura, Hachioji (JP); Eiji Yamamoto, Musashimurayama (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 136 days.

(21) Appl. No.: 14/247,705

(22) Filed: Apr. 8, 2014

(65) Prior Publication Data
US 2014/0218893 A1    Aug. 7, 2014

Related U.S. Application Data

(63) Continuation of application No. PCT/JP2012/075993, filed on Oct. 5, 2012.

(30) Foreign Application Priority Data

Oct. 11, 2011    (JP) .................. 2011-224114

(51) Int. Cl.
| | | |
|---|---|---|
| *F21V 9/16* | (2006.01) | |
| *F21V 8/00* | (2006.01) | |
| *F21Y 101/02* | (2006.01) | |

(52) U.S. Cl.
CPC ............... *F21V 9/16* (2013.01); *G02B 6/0008* (2013.01); *F21Y 2101/025* (2013.01)

(58) Field of Classification Search
CPC .......... H01L 33/504; F21V 9/00; F21V 9/08; F21V 9/083; F21V 9/16
See application file for complete search history.

(56) References Cited

U.S. PATENT DOCUMENTS 8,251,528 B2 * 8/2012 Kim .................... H01L 33/501
257/98
2001/0033135 A1  10/2001 Duggal et al.
(Continued)

FOREIGN PATENT DOCUMENTS

| EP | 1 672 754 A2 | 6/2006 |
|---|---|---|
| EP | 2 074 934 A2 | 7/2009 |

(Continued)

OTHER PUBLICATIONS

Extended Supplementary European Search Report dated Jun. 10, 2015 from related European Application No. 12 84 0415.9.
(Continued)

*Primary Examiner* — Robert May
(74) *Attorney, Agent, or Firm* — Scully, Scott, Murphy & Presser, PC

(57) ABSTRACT

A light source device includes a first excitation light source which emits first excitation light having a wavelength in a first wavelength region, a first optical member, a second optical member and a holding member which holds the first optical member and the second optical member. The first optical member converts at least part of the first excitation light to emit first wavelength converted light, and increase divergence angle of the transmitted first excitation light by a first incremental angle. A second optical member is disposed in a region including an optical axis of the first excitation light, and increases the divergence angle of the transmitted first excitation light by a second incremental angle larger than the first incremental angle.

21 Claims, 7 Drawing Sheets

(56) References Cited

U.S. PATENT DOCUMENTS

| | | | |
|---|---|---|---|
| 2008/0080165 A1* | 4/2008 | Kim | C09K 11/7734 362/84 |
| 2009/0026908 A1 | 1/2009 | Bechtel et al. | |
| 2011/0176290 A1* | 7/2011 | Nishio | G02B 6/262 362/84 |
| 2013/0094179 A1* | 4/2013 | Dai | H05B 33/14 362/84 |

FOREIGN PATENT DOCUMENTS

| | | |
|---|---|---|
| JP | 2007-081215 A | 3/2007 |
| JP | 2007-258019 A | 10/2007 |
| JP | 2009-524914 A | 7/2009 |
| JP | 2009-277734 A | 11/2009 |
| JP | 2010-050404 A | 3/2010 |
| JP | 2010-287680 A | 12/2010 |
| JP | 2011-515848 A | 5/2011 |
| JP | 2011-150857 A | 8/2011 |
| WO | WO 2008/105527 A1 | 9/2008 |

OTHER PUBLICATIONS

International Search Report dated Dec. 11, 2012 issued in PCT/JP2012/075993.

International Preliminary Report on Patentability together with the Written Opinion of the International Searching Authority from related International Application No. PCT/JP2012/075993, dated Apr. 24, 2014.

Japanese Office Action dated Jun. 16, 2015 from related Japanese Patent Application No. 2011-224114, together with an English language translation.

\* cited by examiner

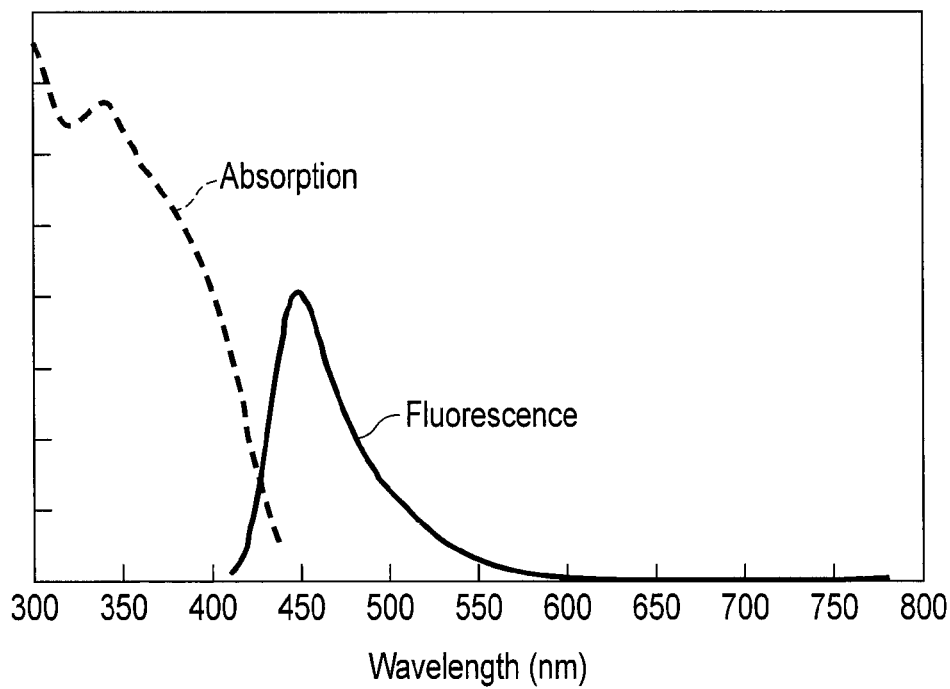
F I G. 4
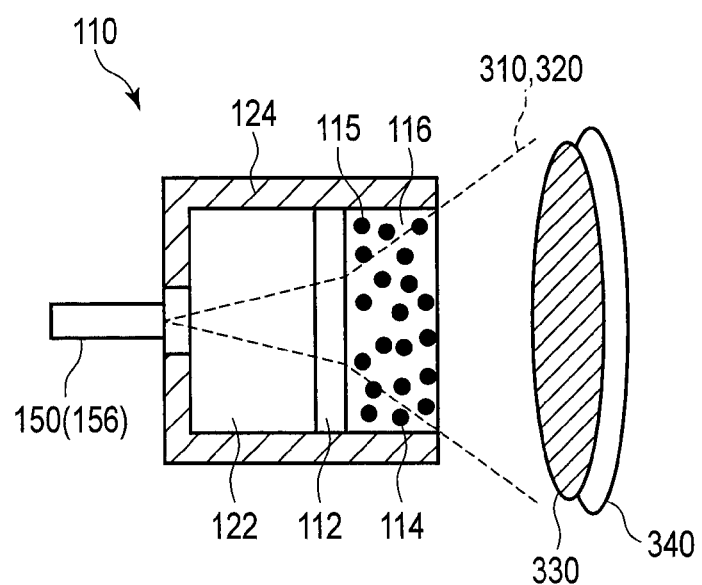
F I G. 5

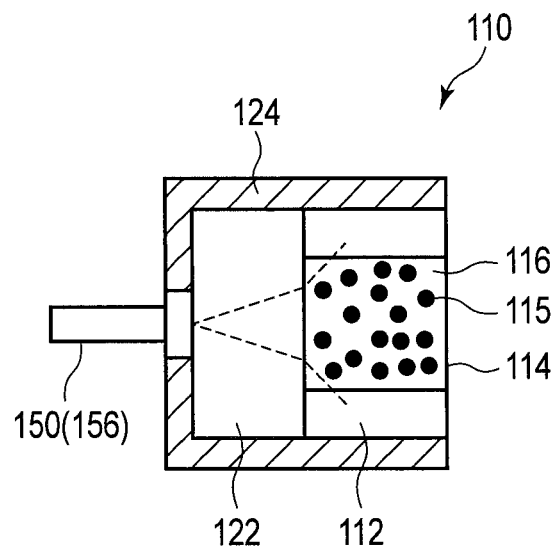
F I G. 10
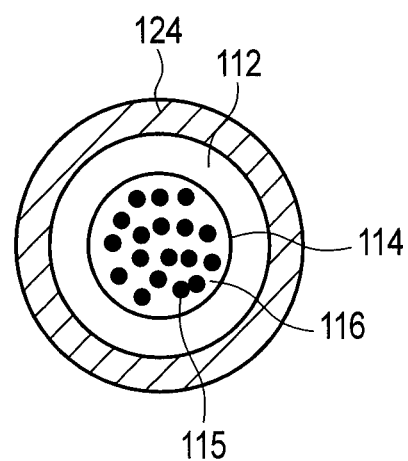
F I G. 11

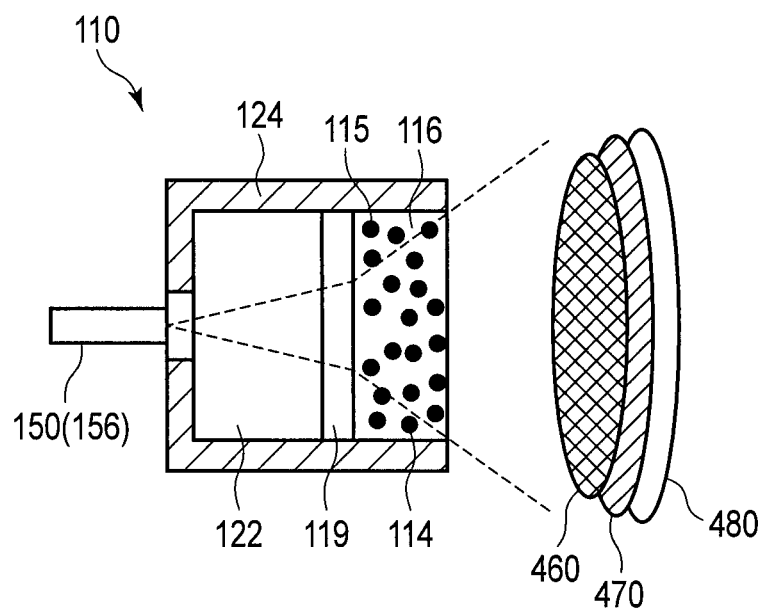
F I G. 12
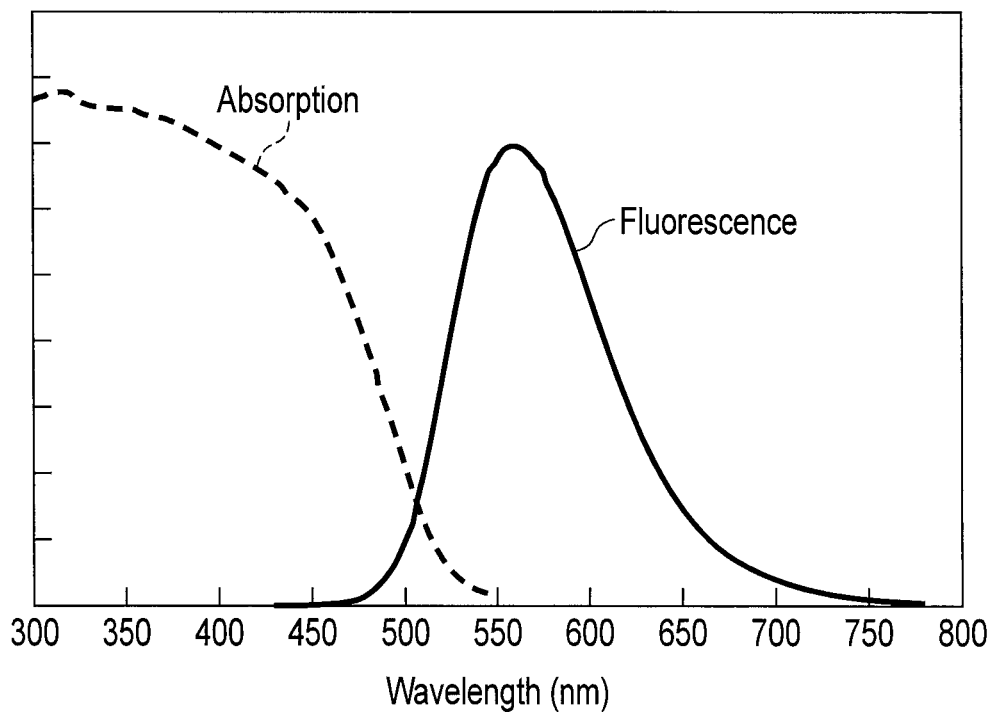
F I G. 13

LIGHT SOURCE DEVICE HAVING OPTICAL MEMBERS FOR CHANGING ONE OR MORE CHARACTERISTICS OF EXCITATION LIGHT FROM AN EXCITATION LIGHT SOURCE

CROSS-REFERENCE TO RELATED APPLICATIONS

This application is a Continuation Application of PCT Application No. PCT/JP2012/075993, filed Oct. 5, 2012 and based upon and claiming the benefit of priority from prior Japanese Patent Application No. 2011-224114, filed Oct. 11, 2011, the entire contents of all of which are incorporated herein by reference.

BACKGROUND OF THE INVENTION

1. Field of the Invention

The present invention relates to a light source device.

2. Description of the Related Art

In general, there has been developed a light source device which emits light from a small solid-state light source, converts this light by a light converting member, and changes illumination light into a desired irradiation pattern or a desired color. For example, International Publication No. 2008/105527 discloses a light source device which is a combination of an LED chip disposed on a metallic substrate, a sealing resin sealing the LED chip, and a fluorescent material disposed on the sealing resin. In this light source device, a plate-shaped fluorescent material disposed on the LED chip is used to convert the wavelength of part of excitation light emitted from the LED chip and then emit fluorescence. In this way, the technique according to International Publication No. 2008/105527 adjusts the illumination light by the excitation light that has passed through the fluorescent material and by the fluorescence emitted from the fluorescent material.

For example, as shown in International Publication No. 2008/105527, the light source device which adjusts the illumination light by the excitation light that has passed through the fluorescent material and by the fluorescence emitted from the fluorescent material has the following problems. That is, the excitation light passing through the fluorescent material is higher in intensity in the vicinity of an optical axis and lower in intensity at a circumferential edge. In contrast, the fluorescence emitted from the fluorescent material is isotropically scattered, and has an isotropic light intensity. Thus, the illumination light emitted from such a light source device is unevenly colored light having a stronger excitation light component in the center and a weaker fluorescent component at the circumferential edge.

BRIEF SUMMARY OF THE INVENTION

An object of the present invention is to provide a light source device which emits illumination light having uniform light distribution characteristics.

To achieve the above described object, according to an aspect of the invention, a light source device includes a first excitation light source configured to emit first excitation light having a wavelength in a first wavelength region; a first optical member configured to absorb at least part of the first excitation light, convert a wavelength of the part of the first excitation light to emit first wavelength converted light, and increase divergence angle of transmitted first excitation light by a first incremental angle; a second optical member disposed in a region including at least an area which includes an optical axis of the first excitation light, light intensity regarding the first excitation light in the area being equal to or more than 1/e times (e is Napier's constant) light intensity on the optical axis, and the second optical member increasing the divergence angle of the transmitted first excitation light by a second incremental angle larger than the first incremental angle; and a holding member which holds the first optical member and the second optical member.

According to the present invention, the divergence angle of the excitation light is adjusted by the second optical member, so that it is possible to provide a light source device which emits illumination light having uniform light distribution characteristics.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a graph showing an example of absorption/fluorescence characteristics of a second wavelength converting member according to the first embodiment;

FIG. 5 is a diagram illustrating the divergence angles of first excitation light and first fluorescence that are derived from the first excitation light in the wavelength converting unit according to the first embodiment;

FIG. 10 is a schematic diagram showing a configuration example of the wavelength converting unit according to a second embodiment;

FIG. 11 is a schematic diagram showing a configuration example of the wavelength converting unit according to the second embodiment;

FIG. 12 is a diagram illustrating a configuration example of the wavelength converting unit according to a third embodiment, and the divergence angle of illumination light emitted from the wavelength converting unit; and FIG. 13 is a graph showing an example of absorption/fluorescence characteristics of a third wavelength converting member according to the third embodiment.

DETAILED DESCRIPTION OF THE INVENTION

[First Embodiment]

Figure 1:
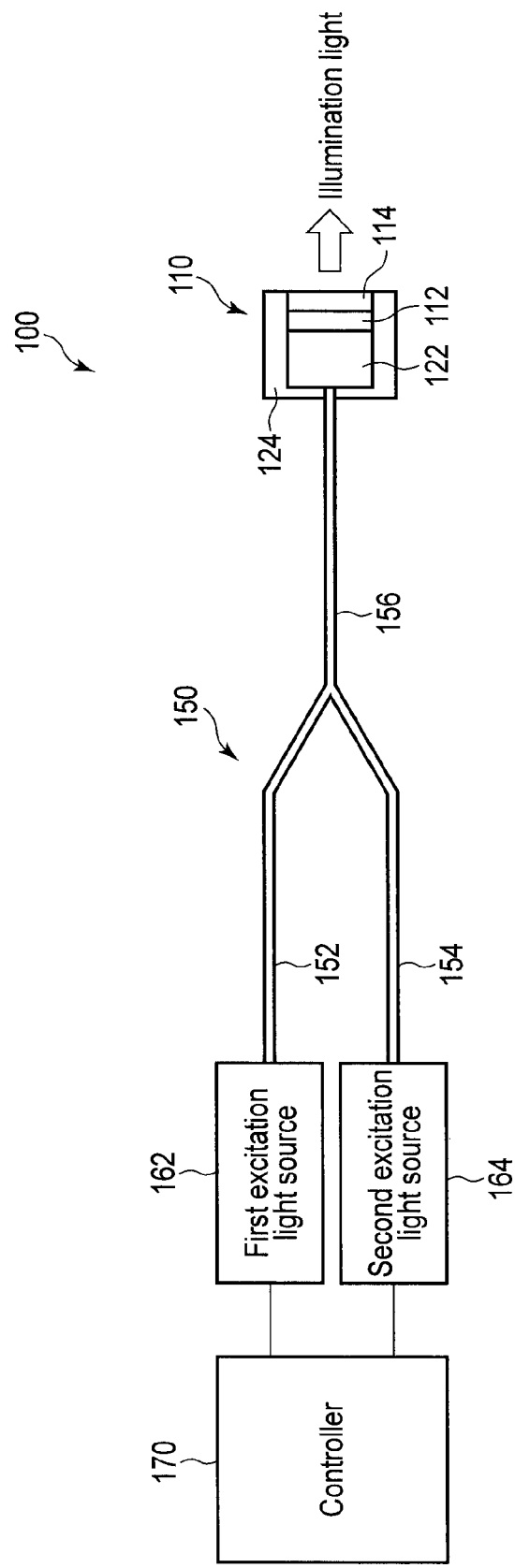
FIG. 1 is a block diagram showing a configuration example of a light source device according to a first embodiment of the present invention.

A first embodiment of the present invention is described with reference to the drawings. The schematic configuration of a light source device 100 according to the present embodiment is shown in FIG. 1. As shown in FIG. 1, the light source device 100 includes a wavelength converting unit 110, an optical coupler 150, a first excitation light source 162, a second excitation light source 164, and a controller 170.

The first excitation light source 162 is a light source which generates excitation light having a wavelength in a first wavelength region. In the present embodiment, the central wavelength in the first wavelength region is 450 nm, and the first excitation light source 162 is a blue laser diode (blue LD) which emits laser light having a wavelength of 450 nm. The excitation light emitted from the first excitation light source 162 is hereinafter referred to as first excitation light. The second excitation light source 164 is a light source which generates excitation light having a wavelength in a second wavelength region. In the present embodiment, the central wavelength in the second wavelength region is 405 nm, and the second excitation light source 164 is a blue-violet laser diode (blue-violet LD) which emits laser light having a wavelength of 405 nm. The excitation light emitted from the second excitation light source 164 is hereinafter referred to as second excitation light.

The controller 170 drives and controls the first excitation light source 162 and the second excitation light source 164. That is, the controller 170 comprises driving circuits which drive the first excitation light source 162 and the second excitation light source 164, respectively. The controller 170 independently controls these driving circuits. The controller 170 is capable of continuous driving or pulsed driving of the first excitation light source 162 and the second excitation light source 164. The controller 170 can also turn on one of the first excitation light source 162 and the second excitation light source 164, and turn off the other. The controller 170 can adjust the ratio between an excitation light intensity of the first excitation light source 162 and an excitation light intensity of the second excitation light source 164 to adjust the color of illumination light, that is, adjust spectrum.

The optical coupler 150 includes a first optical fiber 152, a second optical fiber 154, and a third optical fiber 156. The first optical fiber 152 guides the first excitation light which is the laser light emitted from the first excitation light source 162. The second optical fiber 154 guides the second excitation light which is the laser light emitted from the second excitation light source 164. The light guide paths of the first optical fiber 152 and the second optical fiber 154 are combined into one. That is, the optical coupler 150 combines the first excitation light and the second excitation light. The third optical fiber 156 guides the combined light to the wavelength converting unit 110.

Figure 2:
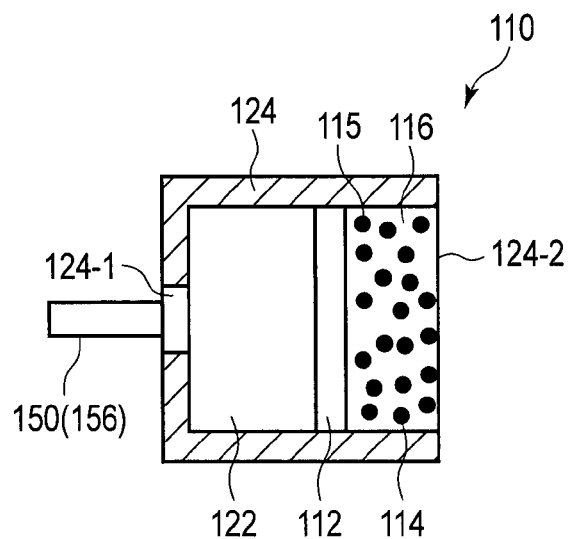
FIG. 2 is a schematic diagram showing a configuration example of a wavelength converting unit according to the first embodiment.

The wavelength converting unit 110 is a wavelength converting unit which receives the first excitation light and the second excitation light guided by the optical coupler 150 and converts part of the first excitation light and the second excitation light to illumination light having different wavelengths. The general structure of the wavelength converting unit 110 is shown in FIG. 2. As shown in FIG. 2, the wavelength converting unit 110 includes a first wavelength converting member 112, a second wavelength converting member 114, a light transmitting member 122, and a holder 124. The light transmitting member 122, the first wavelength converting member 112, and the second wavelength converting member 114 are held by the holder 124 together with the emission end of the optical coupler 150.

That is, the holder 124 has, for example, a cylindrical shape. The holder 124 holds the emission end of the third optical fiber 156 of the optical coupler 150 by the part of an incidence opening 124-1 at one end of the holder 124. The holder 124 has an emission opening 124-2 located opposite to the incidence opening 124-1, and has a continuous through-hole from the incidence opening 124-1 to the emission opening 124-2. An unshown reflecting member is formed on the inner side of this through-hole.

The holder 124 holds the light transmitting member 122, the first wavelength converting member 112, and the second wavelength converting member 114 in order from the emission end of the optical coupler 150 in the emission direction of the excitation light which is emitted from the emission end. Therefore, the excitation light emitted from the emission end of the optical coupler 150 passes through the light transmitting member 122, the first wavelength converting member 112, and the second wavelength converting member 114 in order, and is emitted from the emission opening 124-2 of the holder 124. Thus, the light transmitting member 122, the first wavelength converting member 112, and the second wavelength converting member 114 each have, for example, a columnar shape with a diameter smaller than the diameter of the through-hole of the holder 124. The shape of the holder 124 is cylindrical in the present embodiment, but is not limited to this shape. For example, the holder 124 may have such a shape as a circular cone in which the incidence opening is at the top and the emission opening is at the bottom.

The light transmitting member 122 has the property of transmitting the first excitation light and the second excitation light emitted from the emission end of the optical coupler 150, and the fluorescence emitted from the first wavelength converting member 112 and the second wavelength converting member 114. The light transmitting member 122 is made of, for example, glass or a silicone resin having a high transmittance. In the wavelength converting unit 110, the light transmitting member 122 has a thickness such that the distance from the emission end of the optical coupler 150 to the first wavelength converting member 112 is a desired distance.

In the first wavelength converting member 112, the surface on the side of the light transmitting member 122 is referred to as a light receiving surface, and the surface on the side of the second wavelength converting member 114 is referred to as an emission surface. In the second wavelength converting member 114, the surface on the side of the first wavelength converting member 112 is referred to as a light receiving surface, and the surface opposite to this light receiving surface is referred to as an emission surface. The emission surface of the second wavelength converting member 114 is configured to be flush with the end face of the emission opening 124-2 of the holder 124.

In the present embodiment, for example, a fluorescent material having a composition represented by $Y_3Al_5O_{12}$:Ce (hereinafter referred to as YAG) is used for the first wavelength converting member 112. The first wavelength converting member 112 is made of polycrystallized YAG ceramics. YAG ceramics have a property of hardly diffusing transmitted excitation light. Instead of YAG ceramics, it is also possible to use YAG single crystal, or a ceramic fluorescent material such as LAG:Ce or TAG:Ce for the first wavelength converting member 112. Part of the excitation light which has entered the first wavelength converting member 112 is absorbed in the first wavelength converting member 112. The absorbed light is wavelength converted, and then isotropically emitted from the first wavelength converting member 112 as fluorescence. On the other hand, the excitation light which has not been absorbed in the first wavelength converting member 112 passes through the first wavelength converting member 112.

The second wavelength converting member 114 includes a fluorescent material 115 and a sealing material 116. The fluorescent material 115 is, for example, a powder fluorescent material including $(Sr, Ca, Ba, Mg)_{10}(PO_4)_6Cl_2$:Eu (hereinafter referred to as SCA). Instead of SCA, it is also possible to use, for example, $BaMgAl_{10}O_{17}$:Eu or $BaMgAl_{10}O_{17}$:Eu,Mn.

The average particle diameter of the fluorescent material 115 is, for example, 4.5 μm. This fluorescent material 115 is dispersed in the sealing material 116. Here, the sealing material 116 is, for example, a transparent resin such as a silicone resin. The refractive index of the fluorescent material 115 is higher than the refractive index of the sealing material 116. Having the configuration in which the powder fluorescent material 115 is dispersed in the transparent sealing material 116, the second wavelength converting member 114 also functions as a diffusing member. That is, part of the excitation light which has entered the second wavelength converting member 114 is absorbed in the powder fluorescent material 115. The absorbed light is wavelength converted, and then emitted from the fluorescent material 115 as fluorescence. Here, the fluorescence is isotropically emitted from the fluorescent material 115 in all directions. On the other hand, the excitation light which has not been absorbed in the fluorescent material 115 is scattered by the fluorescent material 115 and then emitted from the second wavelength converting member 114 with a predetermined divergence angle. In this case, the difference between the divergence angle of the light which has entered the second wavelength converting member 114 and the divergence angle of the light emitted from the second wavelength converting member 114, that is, an incremental angle of the divergence angle is determined by, for example, the particle diameter of the fluorescent material 115, the concentration of the fluorescent material 115 compared with the sealing material 116, the refractive indexes of the fluorescent material 115 and the sealing material 116, and the thickness of the whole second wavelength converting member 114.

The particle diameter of the fluorescent material 115 is preferably about 1/10 of the wavelength of the excitation light to about 1000 times. In particular, the divergence angle can be increased if the particle diameter of the fluorescent material 115 is between a particle diameter substantially equal to the wavelength of the excitation light and about 100 times the wavelength. The concentration of the fluorescent material 115 compared with the sealing material 116 can be widely adjusted, for example, between about 0.1 weight percent and about 70 weight percent. For example, when the particle diameter of the fluorescent material 115 is between a particle diameter substantially equal to the wavelength and about 100 times the wavelength, the divergence angle is easily adjusted if the concentration of the fluorescent material 115 compared with the sealing material 116 is between 5 weight percent and about 50 weight percent.

For example, wavelength converting characteristics should preferentially be taken into consideration to select the refractive indexes of the fluorescent material 115 and the sealing material 116. When the refractive index of the fluorescent material 115 is set to a relatively high value of, for example, 1.7 or more, any transparent resin may be used for the sealing material 116. When the refractive index of the fluorescent material 115 is set to a relatively low value of less than 1.7, a transparent resin having a refractive index of, for example, 1.5 or less is preferably used for the sealing material 116. The difference of refractive index between the fluorescent material 115 and the sealing material 116 is preferably more than about 0.2 because the divergence angle is easily increased. A predetermined concentration of a filler which diffuses the excitation light without wavelength conversion may be diffused in the sealing material 116 so that the divergence angle of the excitation light will be a desired angle.

Figure 3:
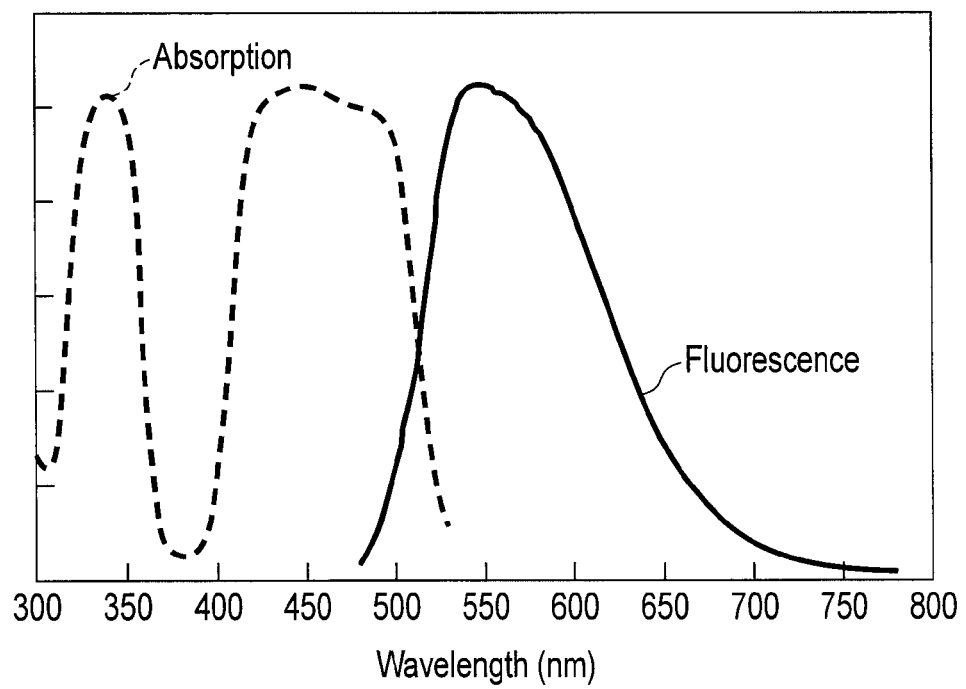
FIG. 3 is a graph showing an example of absorption/fluorescence characteristics of a first wavelength converting member according to the first embodiment.

Absorption/fluorescence characteristics of the first wavelength converting member 112 are shown in FIG. 3. Absorption/fluorescence characteristics of the second wavelength converting member 114 are shown in FIG. 4. Here, in FIG. 3 and FIG. 4, broken lines represent the absorption characteristics of the excitation light, and solid lines represent the fluorescence intensity characteristics. As shown in FIG. 3, the first wavelength converting member 112 absorbs the light including the excitation light having a wavelength of 450 nm emitted by the first excitation light source 162, and emits yellow fluorescence having a peak in the vicinity of a wavelength of 550 nm. On the other hand, as shown in FIG. 4, the second wavelength converting member 114 absorbs the light including the excitation light having a wavelength of 405 nm emitted by the second excitation light source 164, and emits blue fluorescence having a peak in the vicinity of a wavelength of 450 nm.

The operation of the light source device 100 according to the present embodiment is described. In accordance with an instruction from a user, the controller 170 controls the on/off of the outputs of the first excitation light source 162 and the second excitation light source 164, and their output intensities. The first excitation light source 162 emits the first excitation light under the control of the controller 170. The second excitation light source 164 emits the second excitation light under the control of the controller 170.

The first excitation light emitted from the first excitation light source 162 enters the wavelength converting unit 110 through the first optical fiber 152 and the third optical fiber 156 of the optical coupler 150. The second excitation light emitted from the second excitation light source 164 enters the wavelength converting unit 110 through the second optical fiber 154 and the third optical fiber 156 of the optical coupler 150.

The behaviors of the first excitation light and the second excitation light which have entered the wavelength converting unit 110 are described. First described is the case in which the first excitation light emitted from the first excitation light source 162 has entered the wavelength converting unit 110. The first excitation light having a wavelength of 450 nm which has passed through the light transmitting member 122 and entered the first wavelength converting member 112 is partly absorbed in the first wavelength converting member 112, as its absorption characteristics are shown in FIG. 3. The wavelength of the first excitation light absorbed in the first wavelength converting member 112 is converted, and yellow fluorescence having a peak in the vicinity of a wavelength of 550 nm is emitted from the first wavelength converting member 112. This yellow fluorescence is hereinafter referred to as first fluorescence. The first fluorescence is isotropically emitted from the first wavelength converting member 112 in all directions.

Part of the first fluorescence enters the second wavelength converting member 114 through the first wavelength converting member 112. The second wavelength converting member 114 hardly absorbs the first fluorescence having a peak in the vicinity of a wavelength of 550 nm, as shown by its absorption characteristics in FIG. 4. The first fluorescence which has been emitted from the first wavelength converting member 112 and emitted in a direction other than the direction of the second wavelength converting member 114 is repeatedly reflected on the inner circumferential surface of the holder 124, and again enters the first wavelength converting member 112. The first wavelength converting member 112 hardly absorbs the first fluorescence having a peak in the vicinity of a wavelength of 550 nm, as shown in FIG. 3. The first fluorescence passes through the first wavelength converting member 112, and enters the second wavelength converting member 114.

On the other hand, the first excitation light which is not absorbed in the first wavelength converting member 112 is hardly scattered in the first wavelength converting member 112 and passes through the first wavelength converting member 112 as described above, and then enters the second wavelength converting member 114. The second wavelength converting member 114 hardly absorbs the first excitation light having a peak in the vicinity of a wavelength of 450 nm, as shown by its absorption characteristics in FIG. 4.

The first fluorescence and the first excitation light which are hardly absorbed in the second wavelength converting member 114 are scattered by the fluorescent material 115 dispersed in the sealing material 116. The first fluorescence and the first excitation light which have collided with the inner circumferential surface of the holder 124 are reflected by this inner circumferential surface. Thus, the first fluorescence and the first excitation light are emitted in various directions from the emission surface of the second wavelength converting member 114. That is, the first fluorescence and the first excitation light are emitted from the wavelength converting unit 110 with a wide divergence angle. In other words, the divergence angles of the first fluorescence and the first excitation light are increased by the second wavelength converting member 114.

Here, the first fluorescence is emitted from the first wavelength converting member 112 in various directions, and enters the second wavelength converting member 114 from various directions. Therefore, the first fluorescence emitted from the emission surface of the second wavelength converting member 114 has a wide divergence angle. The first excitation light is scattered by the second wavelength converting member 114. Therefore, the first excitation light emitted from the emission surface of the second wavelength converting member 114 has a wide divergence angle. Here, as shown in FIG. 5, the particle diameter and concentration of the fluorescent material 115 in the second wavelength converting member 114 are adjusted so that a divergence angle 310 of the first excitation light emitted from the emission surface of the second wavelength converting member 114 is substantially equal to a divergence angle 320 of the first fluorescence, that is, an irradiation region 330 by the first excitation light is substantially equal to an irradiation region 340 by the first fluorescence.

The first excitation light which has not been absorbed in the first wavelength converting member 112 and has passed through the first wavelength converting member 112 has the highest intensity on its optical axis, and is lower in intensity in peripheral parts. Here, the incidence surface of the second wavelength converting member 114 is larger than at least an incidence range of the first excitation light in which the first excitation light that has passed through the first wavelength converting member 112 has a light intensity equal to or more than 1/e times (e is Napier's constant) the intensity on the optical axis. According to this design, most of the first excitation light which has passed through the first wavelength converting member 112 can directly enter the second wavelength converting member 114 through the emission surface of the first wavelength converting member 112.

Thus, for example, the first excitation light source 162 functions as a first excitation light source which emits first excitation light. For example, the first wavelength converting member 112 functions as a first optical member which absorbs at least part of the first excitation light, converts the wavelength thereof to emit first wavelength converted light, and increases the divergence angle of the transmitted first excitation light by a first incremental angle. For example, the second wavelength converting member 114 functions as a second optical member. The second optical member is disposed in a region including at least an area which includes an optical axis of the first excitation light, light intensity regarding the first excitation light in the area being equal to or more than 1/e times the light intensity on the optical axis of the first excitation light. The second optical member increases the divergence angle of the transmitted first excitation light by a second incremental angle larger than the first incremental angle. For example, the holder 124 functions as a holding member which holds the first optical member and the second optical member. The first wavelength converting member 112 including, for example, the polycrystallized YAG ceramics, the YAG single crystal, or a ceramic fluorescent material such as LAG:Ce or TAG:Ce functions as a first optical member which is a monocrystalline or polycrystalline transparent fluorescent material.

Next described is the case in which the second excitation light emitted from the second excitation light source 164 has entered the wavelength converting unit 110. The second excitation light having a wavelength of 405 nm which has passed through the light transmitting member 122 and entered the first wavelength converting member 112 is hardly absorbed in the first wavelength converting member 112 as its absorption characteristics are shown in FIG. 3, and passes through the first wavelength converting member 112. Here, as described above, the second excitation light is hardly scattered in the first wavelength converting member 112. That is, the second excitation light passes through the first wavelength converting member 112 without changing its divergence angle. The second excitation light which has passed through the first wavelength converting member 112 enters the second wavelength converting member 114.

The second excitation light having a wavelength of 405 nm which has entered the second wavelength converting member 114 is partly absorbed in the second wavelength converting member 114, as shown by its absorption characteristics in FIG. 4. The wavelength of the second excitation light absorbed in the second wavelength converting member 114 is converted, and blue fluorescence having a peak in the vicinity of a wavelength of 450 nm is emitted from the second wavelength converting member 114. This blue fluorescence is hereinafter referred to as second fluorescence. The second fluorescence is isotropically emitted from the second wavelength converting member 114 in all directions.

Part of the second fluorescence emitted in the direction of the first wavelength converting member 112 is absorbed in the first wavelength converting member 112, and the above-mentioned first fluorescence is emitted. The optical path of this first fluorescence is similar to that in the case described above. The second fluorescence which has been emitted in the direction of the first wavelength converting member 112 and passed through the first wavelength converting member 112 without being absorbed therein is reflected by the inner circumferential surface of the holder 124, again enters the first wavelength converting member 112, and is absorbed in the first wavelength converting member 112, and the first fluorescence is emitted, or the second fluorescence passes through the first wavelength converting member 112 and then enters the second wavelength converting member 114.

The second fluorescence which has been emitted from the second wavelength converting member 114 in the direction of the emission opening is diffused by the fluorescent material 115 dispersed in the sealing material 116. The second excitation light which is not absorbed in the second wavelength converting member 114 is also diffused by the fluorescent material 115 dispersed in the sealing material 116.

The second fluorescence and the second excitation light which have collided with the inner circumferential surface of the holder 124 are reflected by this inner circumferential surface. Thus, the second fluorescence and the second excitation light are emitted in various directions from the emission surface of the second wavelength converting member 114. That is, the second fluorescence and the second excitation light are emitted from the wavelength converting unit 110 with a wide divergence angle. In other words, the divergence angles of the second fluorescence and the second excitation light are increased by the second wavelength converting member 114.

Figure 6:
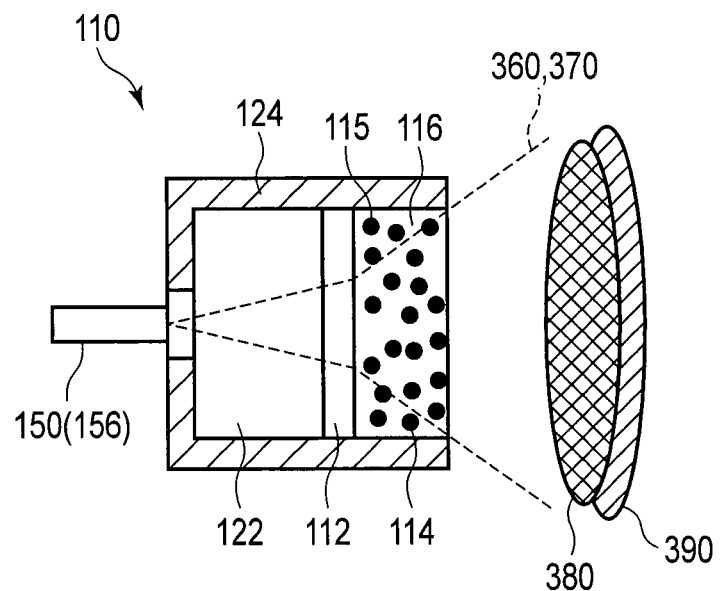
FIG. 6 is a diagram illustrating the divergence angles of second excitation light and second fluorescence that are derived from the second excitation light in the wavelength converting unit according to the first embodiment.

Here, the second fluorescence is emitted from the second wavelength converting member 114 in various directions, and has a wide divergence angle. The second excitation light is scattered by the second wavelength converting member 114, and has a wide divergence angle. As shown in FIG. 6, the particle diameter and concentration of the fluorescent material 115 in the second wavelength converting member 114 are adjusted so that a divergence angle 360 of the second excitation light emitted from the emission surface of the second wavelength converting member 114 is substantially equal to a divergence angle 370 of the second fluorescence, that is, an irradiation region 380 of the second excitation light is substantially equal to an irradiation region 390 of the second fluorescence. Moreover, the particle diameter and concentration of the fluorescent material 115 in the second wavelength converting member 114 are adjusted so that the divergence angle of the first excitation light emitted from the wavelength converting unit 110 is substantially equal to the divergence angle of the second excitation light emitted from the wavelength converting unit 110.

Figure 7:
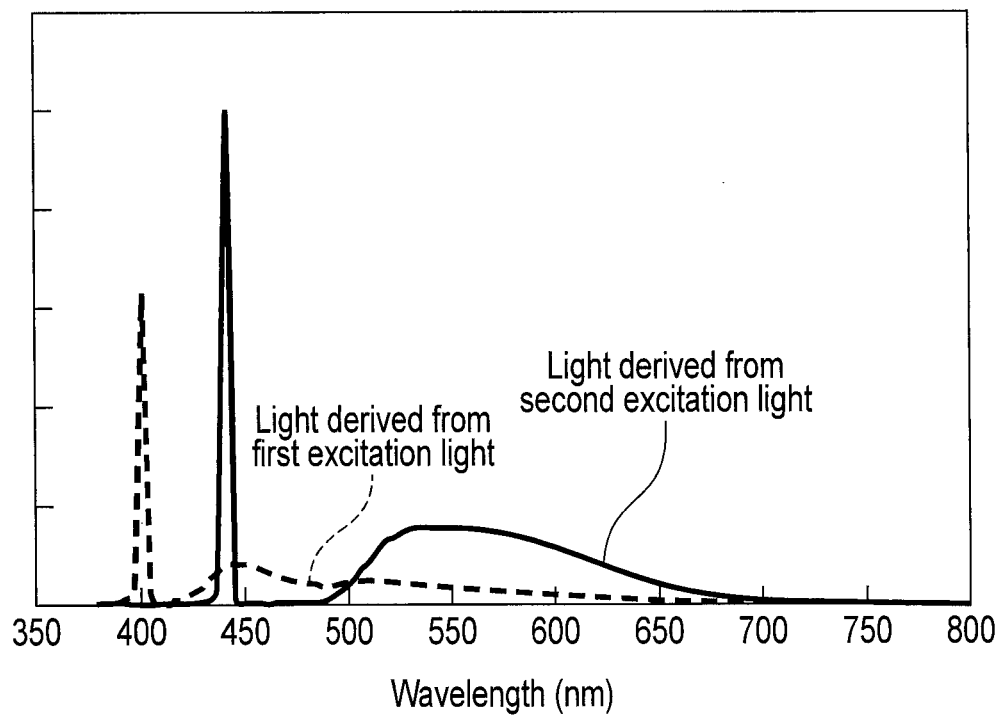
FIG. 7 is a graph showing an example of spectral characteristics of illumination light emitted from the wavelength converting unit according to the first embodiment.

When the first excitation light and/or the second excitation light enter the wavelength converting unit 110 as described above, the first excitation light, the second excitation light, the first fluorescence and/or the second fluorescence having a divergence angle set as described above are emitted from the emission opening of the wavelength converting unit 110. An example spectrum of the light emitted from the wavelength converting unit 110 when both the first excitation light and the second excitation light have entered the wavelength converting unit 110 is shown in FIG. 7. As shown in FIG. 7, the illumination light spectrum of the light source device 100 is a spectrum including the components of the first excitation light, the second excitation light, the first fluorescence, and the second fluorescence. The wavelength converting unit 110, which has the second wavelength converting member 114 located closer to the emission opening than the first wavelength converting member 112, is thus configured so that the absorption of the second excitation light by the first wavelength converting member 112 is reduced and the second excitation light can be emitted with a sufficient intensity.

According to the present embodiment, since the light diffusion by the second wavelength converting member 114 is more than the light diffusion by the first wavelength converting member 112, it is possible to equally adjust the divergence angle 310 of the first excitation light, the divergence angle 360 of the second excitation light, the divergence angle 320 of the first fluorescence, and the divergence angle 370 of the second fluorescence with ease. The divergence angle 310 of the first excitation light emitted from the wavelength converting unit 110, the divergence angle 360 of the second excitation light, the divergence angle 320 of the first fluorescence, and the divergence angle 370 of the second fluorescence can be equal, so that the light source device 100 can emit illumination light that is less unevenly colored.

If the light is greatly diffused by the first wavelength converting member 112, the light diffused by the first wavelength converting member 112 is applied to the inner surface of the holder 124, and light loss through, for example, absorption is greater. Meanwhile, according to the present embodiment, the first wavelength converting member 112 that causes little light diffusion is used. Thus, the energy conversion efficiency of the light source device 100 is high. When the second wavelength converting member 114 is used to diffuse light as in the present embodiment, it is not necessary to additionally provide a light diffusing member to adjust the divergence angle, and the light loss can be reduced. Consequently, the energy conversion efficiency of the light source device 100 is high.

In the configuration according to the present embodiment, the second wavelength converting member 114 and the first wavelength converting member 112 that are fluorescent materials having different absorption/fluorescence characteristics are disposed in the wavelength converting unit 110, and the first excitation light and the second excitation light having two different wavelengths are applied to the second wavelength converting member 114 and the first wavelength converting member 112. This configuration permits one light source device to adjust the color of light to be emitted by changing the light intensity ratio between the first excitation light and the second excitation light.

According to the present embodiment, the difference between the wavelength of the excitation light and the wavelength of the fluorescence is small in the fluorescent materials used for the first wavelength converting member 112 and the second wavelength converting member 114, so that energy loss resulting from wavelength conversion can be reduced. As a result, the energy conversion efficiency of the light source device 100 is higher.

When the sizes of the surfaces of the first wavelength converting member 112 and the second wavelength converting member 114 perpendicular to the optical axes of the first excitation light and the second excitation light are equal to or more than the range in which light having an intensity equal to or more than 1/e times the intensity on the optical axes of the first excitation light and the second excitation light enters, most of the first excitation light and the second excitation light enters.

According to the present embodiment described above, the second wavelength converting member 114 includes the fluorescent material which converts the wavelength. In contrast, when the first excitation light alone is used, a dispersing element such as alumina that only has the function to scatter light may be used. In this case, it is possible to configure a light source device which allows the divergence angles of the first excitation light and the first fluorescence to be the same and thereby emits the first excitation light, the second excitation light, and the first fluorescence that are not unevenly colored.

[Modifications of the First Embodiment]

Figure 8:
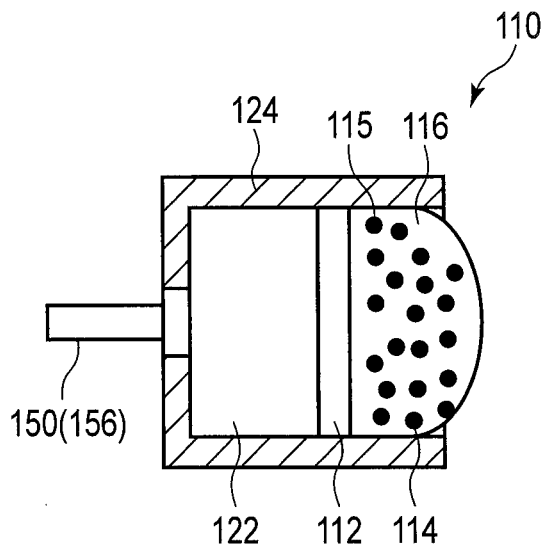
FIG. 8 is a schematic diagram showing a configuration example of the wavelength converting unit according to a first modification of the first embodiment.

Modifications of the first embodiment are described. Here, parts different from those in the first embodiment are described, and the same parts are indicated by the same reference signs and are not described. The first modification is initially described. A schematic diagram of the configuration of the wavelength converting unit 110 according to the present modification is shown in FIG. 8. As shown in FIG. 8, the wavelength converting unit 110 according to the present modification is different from the wavelength converting unit 110 according to the first embodiment in the thickness of the second wavelength converting member 114. The second wavelength converting member 114 according to the present modification is thicker on the optical axes of the first excitation light and the second excitation light, and has a convex emission surface.

The first excitation light and the second excitation light emitted from the emission end of the optical coupler 150 (the third optical fiber 156) have the strongest light intensity on their optical axes. The second wavelength converting member 114 is shaped to be thickest on the optical axes of the first excitation light and the second excitation light, so that the first excitation light and the second excitation light are sufficiently diffused. This shape also allows a higher rate of the wavelength conversion of the second excitation light.

Although the emission surface of the second wavelength converting member 114 is projecting outside the emission opening of the holder 124 in FIG. 8, this is not restrictive. Although the emission surface is convex in the example shown in FIG. 8, the shape of the second wavelength converting member 114 is not limited to the shape shown in FIG. 8 as long as the second wavelength converting member 114 is thicker in the vicinity of the optical axes than in the circumferential edge. The incidence surface may be convex.

Figure 9:
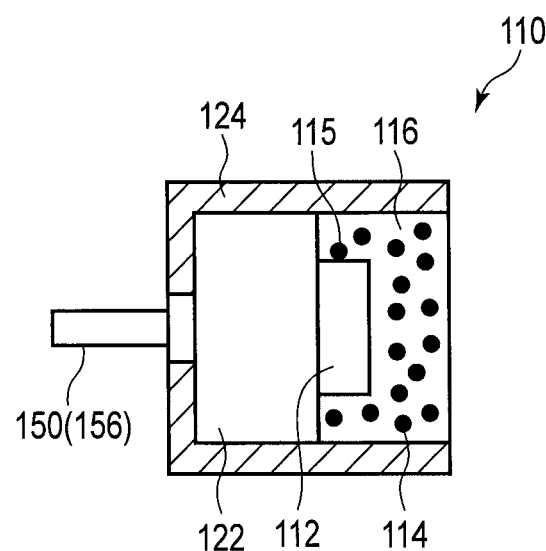
FIG. 9 is a schematic diagram showing a configuration example of the wavelength converting unit according to a second modification of the first embodiment.

Now, the second modification is described. A schematic diagram of the configuration of the wavelength converting unit 110 according to the present modification is shown in FIG. 9. As shown in FIG. 9, the wavelength converting unit 110 according to the present modification comprises, on the optical axes of the first excitation light and the second excitation light, the first wavelength converting member 112 smaller in diameter than the second wavelength converting member 114. The second wavelength converting member 114 is disposed to also cover the side surface of the first wavelength converting member 112.

Regarding the second excitation light which has entered with a predetermined divergence angle, the central part close to the optical axis enters the first wavelength converting member 112, and the circumferential edge part far from the optical axis directly enters the second wavelength converting member 114. The second excitation light which has been directly applied to the second wavelength converting member 114 is wavelength converted and is diffused by the second wavelength converting member 114. Some of the second excitation light again enters the first wavelength converting member 112, and the rest passes through the second wavelength converting member 114 and is then emitted from the emission opening of the wavelength converting unit 110.

According to the present modification, the diameter of the first wavelength converting member 112 disposed on the optical axes of the excitation lights is small, so that a lower rate of the second fluorescence which has been wavelength converted from the second excitation light again enters the first wavelength converting member 112. As a result, the rate of the second fluorescence to be secondarily absorbed in the first wavelength converting member 112 is lower, and the rate of the second fluorescence can be higher.

[Second Embodiment]

A second embodiment is described. Here, parts different from those in the first embodiment are described, and the same parts are indicated by the same reference signs and are not described. A schematic configuration example of the wavelength converting unit 110 according to the present embodiment is shown in FIG. 10 and FIG. 11. FIG. 10 is a schematic diagram showing the cross section of the wavelength converting unit 110. FIG. 11 is a schematic diagram showing the plane of the wavelength converting unit 110 seen from the side of the emission opening.

As shown in FIG. 10 and FIG. 11, the second wavelength converting member 114 is disposed on the optical axes of the first excitation light and the second excitation light emitted from the emission end of the optical coupler 150 (the third optical fiber 156). The second wavelength converting member 114 is columnar. Here, as the divergence angles of the first excitation light and the second excitation light are indicated by broken lines in FIG. 10, the diameter of the second wavelength converting member 114 is larger than a beam spot diameter at which the first excitation light and the second excitation light enter the second wavelength converting member 114. The first wavelength converting member 112 having a hollow and columnar shape is disposed to cover the outer circumferential side surface of the second wavelength converting member 114.

The first excitation light and the second excitation light emitted from the emission end of the optical coupler 150 (the third optical fiber 156) pass through the light transmitting member 122, and enter the second wavelength converting member 114. The wavelength of some of the second excitation light is converted by the second wavelength converting member 114, and the second fluorescence is emitted. The rest of the second excitation light passes through the second wavelength converting member 114 while being scattered therein. On the other hand, the first excitation light which has entered the second wavelength converting member 114 is substantially not wavelength converted and is scattered, and is then partly emitted from the emission opening of the wavelength converting unit 110. The first excitation light which has been scattered in the second wavelength converting member 114 and then entered the first wavelength converting member 112 is wavelength converted, and the first fluorescence is then emitted.

The second wavelength converting member 114 having a high ability to diffuse the first excitation light and the second excitation light is located in the region close to the optical axes of the first excitation light and the second excitation light, and the first wavelength converting member 112 having a low diffusing ability is located in the outer circumferential part of the first wavelength converting member 112, so that most of the first excitation light and the second excitation light enter the second wavelength converting member 114. As a result, the first excitation light and the second excitation light are diffused by the second wavelength converting member 114. Thus, according to the present embodiment, light having a wide divergence angle can be emitted.

The first excitation light is wavelength converted by the first wavelength converting member 112 after being diffused by the second wavelength converting member 114. Therefore, places where heat is generated by the wavelength conversion are dispersed, so that it is possible to prevent the first wavelength converting member 112 from being locally increased in temperature. Since the first wavelength converting member 112 and the second wavelength converting member 114 are out of contact with each other on the optical axes of the first excitation light and the second excitation light, the influence of the wavelength conversion loss heat generated in the second wavelength converting member 114 on the first wavelength converting member 112 can be reduced. Consequently, temperature quenching in the first wavelength converting member 112 can be inhibited.

[Third Embodiment]

A third embodiment is described. Here, parts different from those in the first embodiment are described, and the same parts are indicated by the same reference signs and are not described. A schematic configuration example of the wavelength converting unit 110 according to the present embodiment is shown in FIG. 12. As shown in FIG. 12, the light transmitting member 122, a third wavelength converting member 119, and the second wavelength converting member 114 are arranged in the holder 124 of the wavelength converting unit 110 in order in the traveling direction of the first excitation light and the second excitation light from the side of the emission end of the optical coupler 150.

An example of absorption/fluorescence characteristics of the third wavelength converting member 119 is shown in FIG. 13. As shown in FIG. 13, the third wavelength converting member 119 has the absorption characteristics for the wavelength region of the first excitation light and the wavelength region of the second excitation light, and emits fluorescence having a peak in the vicinity of a wavelength of 550 nm. Hereinafter, the fluorescence having the peak in the vicinity of a wavelength of 550 nm is referred to as third fluorescence. The material of this third wavelength converting member 119 is, for example, a orthosilicate fluorescent material. Although not shown in FIG. 12, the third wavelength converting member 119 has a structure in which a powder fluorescent material is dispersed in a sealing material.

According to the present embodiment, the first excitation light is partly absorbed in the third wavelength converting member 119, and the third fluorescence is isotropically emitted in all directions. The third fluorescence is hardly absorbed in the second wavelength converting member 114. Thus, the third fluorescence is applied to an irradiation region 480 with a wide divergence angle from the emission opening of the wavelength converting unit 110.

On the other hand, the first excitation light which has passed through the third wavelength converting member 119 is not absorbed in the second wavelength converting member 114, and is diffused in the second wavelength converting member 114, and is then applied to an irradiation region 460 of the first excitation light with a wide divergence angle from the emission opening of the wavelength converting unit 110.

The second excitation light is partly absorbed in the third wavelength converting member 119, and the third fluorescence is isotropically emitted in all directions. The third fluorescence is applied to the irradiation region 480 of the third fluorescence with a wide divergence angle from the emission opening of the wavelength converting unit 110 as described above. On the other hand, the second excitation light which has passed through the third wavelength converting member 119 has its wavelength converted by the second wavelength converting member 114, and the second fluorescence is isotropically emitted in all directions. As a result, the second fluorescence is applied to an irradiation region 470 of the second fluorescence with a wide divergence angle from the emission opening of the wavelength converting unit 110.

According to the present embodiment, the first excitation light, the second excitation light, the second fluorescence, and the third fluorescence can be emitted from the wavelength converting unit 110 with a properly unified divergence angle.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source device comprising:
    a first excitation light source configured to emit first excitation light having a wavelength in a first wavelength region;
    a first optical member configured to absorb at least part of the first excitation light, convert a wavelength of the part of the first excitation light to emit first wavelength converted light, and increase a divergence angle of transmitted first excitation light by a first incremental angle;
    a second optical member configured to increase the divergence angle of the transmitted first excitation light by a second incremental angle larger than the first incremental angle; and
    a holding member which holds the first optical member and the second optical member, wherein
    the second optical member includes a powder material and a transparent member which transmits light,
    an absorption rate of the first excitation light of the powder material is less than a predetermined value, and
    the powder material is dispersed in the transparent member.

2. The light source device according to claim 1, wherein the first optical member includes a transparent fluorescent material, and
    the powder material absorbs light having a wavelength in a second wavelength region different from the first wavelength region, and converts the wavelength of the light having the wavelength in the second wavelength region to emit second wavelength converted light.

3. The light source device according to claim 2, further comprising
    an optical fiber configured to guide the first excitation light, wherein
    the holding member comprises an incidence portion through which the first excitation light guided by the optical fiber enters, and an emission portion which emits at least part of the first excitation light and the first wavelength converted light, both the first optical member and the second optical member are disposed on an optical axis of the first excitation light entering through the incidence portion, and the first optical member is located closer to the incidence portion than the second optical member.

4. The light source device according to claim 3, wherein a wavelength of the second wavelength converted light is shorter than a wavelength of the first wavelength converted light.

5. The light source device according to claim 3, wherein the thickness of the second optical member in an optical axis direction increases towards the optical axis.

6. The light source device according to claim 3, wherein
the first optical member and the second optical member are columnar,
a diameter of the second optical member is larger than a diameter of the first optical member, and
a thickness of the second optical member in an optical axis direction is greater than a thickness of the first optical member in the optical axis direction.

7. The light source device according to claim 2, wherein
the holding member comprises an incidence portion through which the first excitation light enters, and an emission portion which emits the first wavelength converted light, and
the first optical member and the second optical member are arranged to divide a surface perpendicular to an optical axis of the first excitation light which enters through the incidence portion.

8. The light source device according to claim 7, wherein the second optical member is disposed on the optical axis of the first excitation light and the first optical member is not disposed on the optical axis of the first excitation light.

9. The light source device according to claim 8, wherein a surface of the second optical member through which the first excitation light enters is larger than a beam spot diameter of the first excitation light in the surface.

10. The light source device according to claim 2, further comprising a second excitation light source configured to emit second excitation light having a wavelength in the second wavelength region,
wherein the second optical member is configured to absorb at least part of the second excitation light, and convert the wavelength of the second excitation light to emit the second wavelength converted light.

11. The light source device according to claim 10, wherein
the first excitation light and the second excitation light are combined by an optical coupler,
the holding member comprises an incidence portion through which the first excitation light and the second excitation light that have been combined enter, and an emission portion which emits the first excitation light, the second excitation light, the first wavelength converted light, and the second wavelength converted light, and
an optical axis of the first excitation light entering through the incidence portion corresponds to an optical axis of the second excitation light.

12. The light source device according to claim 11, wherein
at least one of the first excitation light and the second excitation light pass through the first optical member and the second optical member, and are then emitted from the emission portion, and
the divergence angle of the first excitation light or the second excitation light, the divergence angle of the first wavelength converted light, and the divergence angle of the second wavelength converted light emitted from the emission portion are adjusted to be equal to one another.

13. The light source device according to claim 2, wherein the first optical member includes a single crystal or polycrystalline fluorescent material.

14. The light source device according to claim 1, wherein
the first optical member also absorbs part of light having a wavelength in a second wavelength region different from the first wavelength region, and converts the wavelength of the part of the light having the wavelength in the second wavelength region to emit the first wavelength converted light,
the second optical member includes a powder fluorescent material and a transparent member which transmits light, the powder fluorescent material absorbing the light having the wavelength in the second wavelength region and converting the wavelength of the light having the wavelength in the second wavelength region to emit second wavelength converted light, and
the powder fluorescent material is dispersed in the transparent member.

15. The light source device according to claim 1, wherein
the powder material includes diffused particles, and
the transparent member transmits the first excitation light and the first wavelength converted light,
the diffused particles includes one of
reflective diffused particles which reflect at least one of the first excitation light and the first wavelength converted light, and
transmissive diffused particles which have a refractive index higher than a refractive index of the transparent member and transmit at least one of the first excitation light and the first wavelength converted light.

16. The light source device according to claim 1, wherein
the first excitation light passes through the first optical member and the second optical member, and are then emitted from an emission portion, and
a diffusion characteristic of the second optical member is determined based on the divergence angle of the first excitation light and the divergence angle of the first wavelength converted light emitted from the emission portion.

17. The light source device according to claim 1, wherein
the first excitation light passes through the first optical member and the second optical member, and are then emitted from an emission portion, and
the divergence angle of the first excitation light, and the divergence angle of the first wavelength converted light emitted from the emission portion are adjusted to be substantially equal to one another.

18. The light source device according to claim 1, wherein the second optical member hardly absorbs the first excitation light.

19. The light source device according to claim 1, wherein the second optical member is disposed in a region including at least an area which includes an optical axis of the first excitation light, light intensity regarding the first excitation light in the area being equal to or more than $1/e$ times light intensity on the optical axis, where e is Napier's constant.

20. A light source device comprising:
a first excitation light source configured to emit first excitation light having a wavelength in a first wavelength region;
a first optical member configured to absorb at least part of the first excitation light, convert a wavelength of the part of the first excitation light to emit first wavelength converted light, and increase a divergence angle of transmitted first excitation light by a first incremental angle;
a second optical member configured to increase the divergence angle of the transmitted first excitation light by a second incremental angle larger than the first incremental angle; and
a holding member which holds the first optical member and the second optical member, wherein
the holding member comprises an incidence portion through which the first excitation light enters, and an emission portion which emits the first wavelength converted light,
the first optical member and the second optical member are arranged to divide a surface perpendicular to an optical axis of the first excitation light which enters through the incidence portion, and
the second optical member is disposed on the optical axis of the first excitation light and the first optical member is not disposed on the optical axis of the first excitation light.

21. A light source device comprising:
a first excitation light source configured to emit first excitation light having a wavelength in a first wavelength region;
a first optical member configured to absorb at least part of the first excitation light, convert a wavelength of the part of the first excitation light to emit first wavelength converted light, and increase a divergence angle of transmitted first excitation light by a first incremental angle;
a second optical member configured to increase the divergence angle of the transmitted first excitation light by a second incremental angle larger than the first incremental angle;
a holding member which holds the first optical member and the second optical member; and
a second excitation light source configured to emit second excitation light having a wavelength in a second wavelength region, wherein
the second optical member is configured to absorb at least part of the second excitation light, and convert the wavelength of the second excitation light to emit the second wavelength converted light,
the first excitation light and the second excitation light are combined by an optical coupler,
the holding member comprises an incidence portion through which the first excitation light and the second excitation light that have been combined enter, and an emission portion which emits the first excitation light, the second excitation light, the first wavelength converted light, and the second wavelength converted light, and
an optical axis of the first excitation light entering through the incidence portion corresponds to an optical axis of the second excitation light.

* * * * *